United States Patent
Yamada et al.

(10) Patent No.: US 8,291,746 B2
(45) Date of Patent: Oct. 23, 2012

(54) SENSOR

(75) Inventors: Naoki Yamada, Iwakura (JP);
Takayoshi Atsumi, Konan (JP); Takeo Mizui, Konan (JP); Hideya Inukai, Ogaki (JP); Yoshiyasu Fujii, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 576 days.

(21) Appl. No.: 12/503,948

(22) Filed: Jul. 16, 2009

(65) Prior Publication Data
US 2010/0011838 A1  Jan. 21, 2010

(30) Foreign Application Priority Data

Jul. 17, 2008 (JP) ................................ 2008-186025
Jun. 2, 2009 (JP) ................................ 2009-133243

(51) Int. Cl.
G01N 27/28 (2006.01)
G01N 27/403 (2006.01)
(52) U.S. Cl. ...................................... 73/31.05; 73/23.31
(58) Field of Classification Search .................. 204/424, 204/426, 427, 428
See application file for complete search history.

(56) References Cited

U.S. PATENT DOCUMENTS

| 7,562,555 B2 * | 7/2009 | Nishio et al. .................... 73/23.2 |
| 2001/0002651 A1 | 6/2001 | Akatsuka et al. |
| 2003/0136675 A1 | 7/2003 | Ishikawa |
| 2007/0017193 A1 | 1/2007 | Nishio et al. |

FOREIGN PATENT DOCUMENTS

| JP | 2000-249678 A |   | 9/2000 |
| JP | 2002-139473   | * | 5/2002 |
| JP | 2002-181765 A |   | 6/2002 |
| JP | 2002-286682 A |   | 10/2002 |
| JP | 2002-372513 A |   | 12/2002 |
| JP | 2003-043000 A |   | 2/2003 |
| JP | 2003-279530 A |   | 10/2003 |
| JP | 2006-017542 A |   | 1/2006 |

* cited by examiner

*Primary Examiner* — Daniel Larkin
(74) *Attorney, Agent, or Firm* — Sughrue Mion, PLLC

(57) ABSTRACT

A sensor including a tubular casing having an open rear end; and a first elastic member having a through hole so as to introduce ambient air into the casing and disposed so as to block the rear end opening of the casing. The sensor further includes: a holding inner tube that closely contacts an inner peripheral surface of the through hole; a ventilation filter that has permeability and a waterproofing property, the ventilation filter including a filter blocking portion that blocks a rear end opening of the holding inner tube, and a filter tubular portion connected to the filter blocking portion and surrounding at least a portion of an outer peripheral surface of a rear end portion of the holding inner tube in the peripheral direction; and a holding outer tube that includes a ventilation hole, an outer tube blocking portion covering the filter blocking portion, and an outer tube tubular portion connected to the outer tube blocking portion and surrounding at least a portion of the filter tubular portion in the peripheral direction.

7 Claims, 5 Drawing Sheets

// SENSOR

BACKGROUND OF THE INVENTION

1. Field of the Invention

The present invention relates to a sensor that introduces ambient air into the inside of the sensor via a ventilation filter.

2. Description of the Related Art

Conventionally known is a sensor including a long detecting element that detects a gas to be measured, such as $O_2$ or $N_2$, a main fitting that holds the detecting element, and an outer tube that is arranged at the rear end of the main fitting and accommodates a rear end portion of the detecting element therein.

Such a sensor includes a lead wire that is arranged inside the outer tube from outside the outer tube through the rear end opening of the outer tube and is connected to the detecting element, and an elastic member (hereinafter also referred to as a grommet) that is arranged inside the rear end opening of the outer tube so as to hold and cover the radial periphery of the lead wire.

Among sensors configured in this manner, for example, an ambient air introduction type sensor, such as an oxygen sensor, introduces ambient air into the inside of the sensor. The physical quantity of the introduced ambient air serves as the basis for detecting the physical quantity of an object to be measured. Further, a through hole for introducing ambient air into the inside of the sensor is provided in the grommet. Also, a ventilation filter having permeability and a waterproofing property is arranged so as to cover the rear end opening of the through hole. This configuration secures ventilation without allowing moisture to pass into the inside of the sensor through the ventilation filter (for example, refer to Patent Documents 1 and 2).

Patent Document 1 JP-A-2000-249678 (FIG. 2)
Patent Document 2 JP-A-2002-286682 (FIG. 10)

3. Problems to be Solved by the Invention

However, the ventilation filter described in Patent Document 1 is sandwiched between an inner peripheral surface of the through hole provided in the grommet and a tubular insertion member inserted into the through hole, and the end of the ventilation filter is arranged inside the sensor. For this reason, there is a possibility that moisture adhering to the surface of the ventilation filter may enter inside the sensor through the gap between the inner peripheral surface of the through hole and the ventilation filter.

Additionally, the ventilation filter described in Patent Document 2 covers almost the entire upper surface of the grommet, and a protective member is provided so as to cover the ventilation filter. The protective member is fixed between the outer tube and the grommet, and the end of the ventilation filter is arranged in the space between the protective member and the grommet, the space is blocked from the outside. For this reason, when moisture adhering to the ventilation filter seeps into the space between the protective member and the grommet along the surface of the ventilation filter, there is a possibility of the moisture turning around at the end of the ventilation filter, reaching the rear end opening of the through hole through the gap between the upper surface of the grommet and the ventilation filter, and entering inside the sensor.

The invention was made in view of the above problems, and the object of the invention is to provide a technique for preventing moisture adhering to a ventilation filter from entering into the inside of a sensor along the surface of a ventilation filter.

SUMMARY OF THE INVENTION

The above object of the invention has been achieved by providing a sensor comprising: a tubular casing that holds a detecting element extending in an axial direction so as to expose a leading end of the detecting element to a gas to be measured, the tubular casing extending in the axial direction and having an open rear end; and a first elastic member having a through hole that is provided along the axial direction so as to introduce ambient air into the casing and disposed so as to block the rear end opening of the casing, wherein the sensor includes: a holding inner tube that closely contacts an inner peripheral surface of the through hole of the first elastic member, the holding inner tube having a rear end portion that protrudes from a rear end of the first elastic member; a ventilation filter having permeability and a waterproofing property, the ventilation filter including a filter blocking portion that blocks a rear end opening of the holding inner tube, and a filter tubular portion connected to the filter blocking portion and surrounding at least a portion of an outer peripheral surface of the rear end portion of the holding inner tube in the peripheral direction; and a holding outer tube that includes a ventilation hole that is provided along the axial direction, an outer tube blocking portion covering the filter blocking portion, and an outer tube tubular portion connected to the outer tube blocking portion and surrounding at least a portion of the filter tubular portion in the peripheral direction.

BRIEF DESCRIPTION OF THE DRAWINGS

Illustrative aspects of the invention will now be described in detail with reference to the following figures wherein.

DETAILED DESCRIPTION OF THE PREFERRED EMBODIMENTS

Hereinafter, various embodiments of the invention will be described with reference to the drawings. However, the present invention should not be construed as being limited thereto.

First Embodiment

Figure 1:
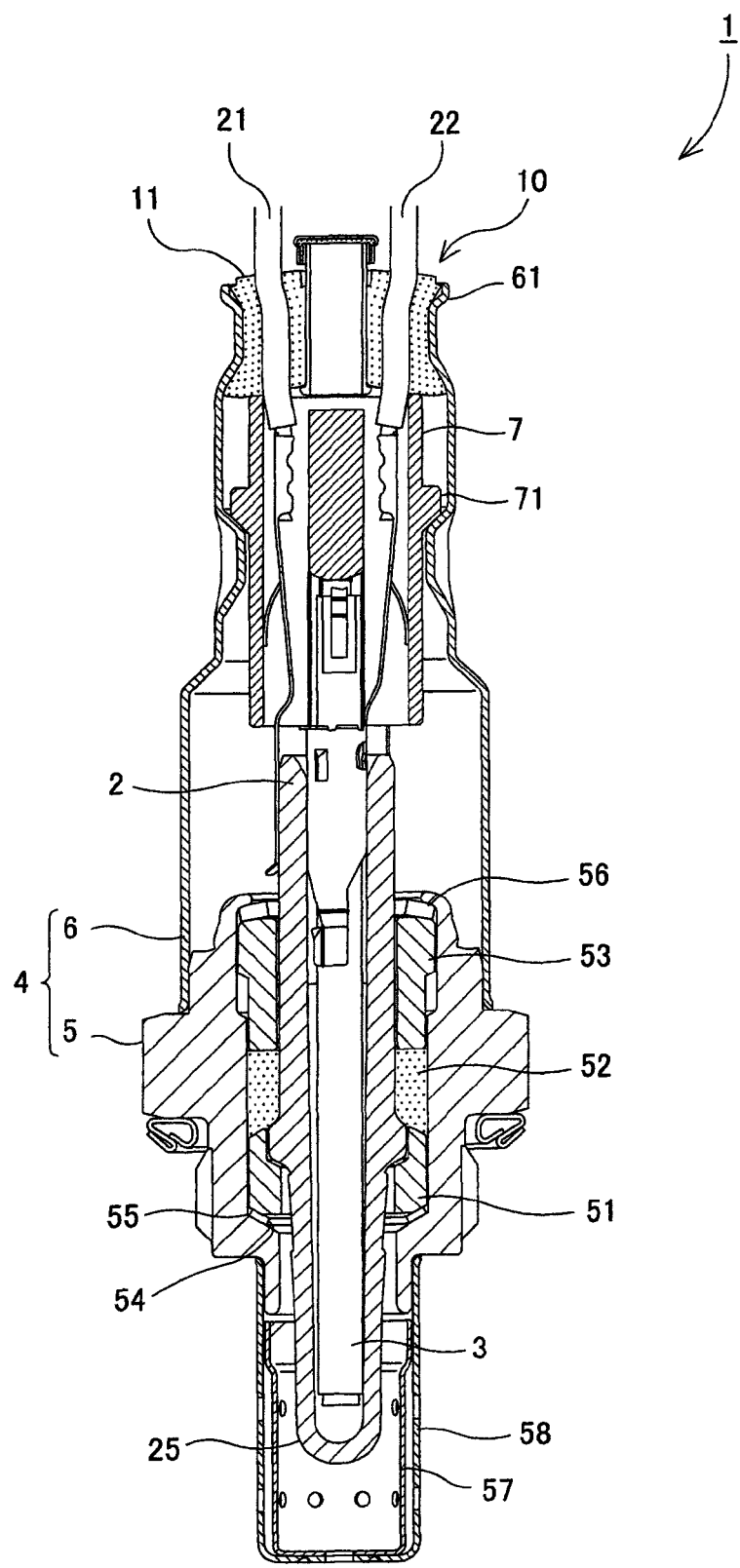
FIG. 1 is a sectional view showing the entire configuration of an oxygen sensor 1.
Figure 2:
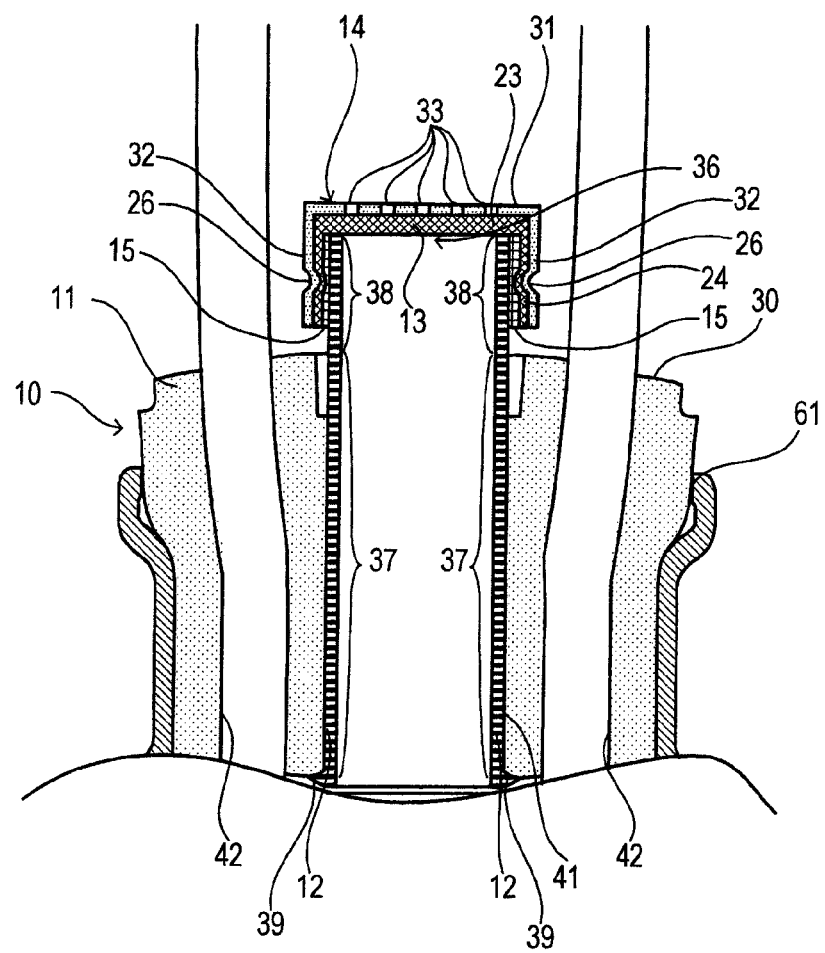
FIG. 2 is a sectional view showing the configuration of a seal unit 10 of a first embodiment.
Figure 3:
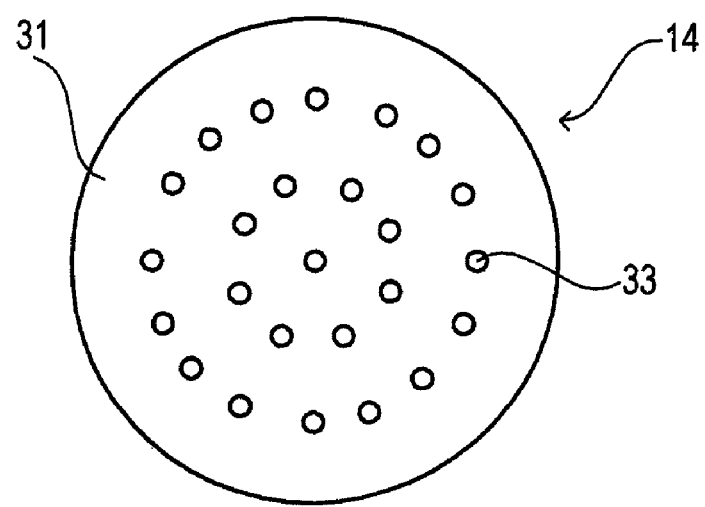
FIG. 3 is a plan view of a holding outer tube 14 of the first embodiment.

FIG. 1 is a sectional view showing the entire configuration of an oxygen sensor 1 of the embodiment to which the invention is applied, FIG. 2 is a sectional view showing the configuration of a seal unit 10, and FIG. 3 is a plan view of a holding outer tube 14.

In addition, in this embodiment, the lower end side of the oxygen sensor 1 in FIG. 1 corresponds to the "leading end side of the sensor," and the upper end side of the oxygen sensor 1 similarly corresponds to the "rear end side of the sensor."

As shown in FIG. 1, the oxygen sensor 1 includes a detecting element 2 comprising a solid electrolyte body in the shape of a hollow shaft having a closed leading end and composed mainly of $ZrO_2$, a shaft-like ceramic heater 3 is arranged within the detecting element 2, and a casing 4 that houses the internal structure of the oxygen sensor 1 and fixes the oxygen sensor 1 to an attachment portion, such as an exhaust pipe and the like.

Among them, the casing 4 includes a metal shell 5 that holds the detecting element 2 to allow detecting portion 25 in the detecting element to protrude into an exhaust pipe or the like, and an outer tube 6 that extends to an upper portion of the metal shell 5 and forms a reference gas space between the outer tube and the detecting element 2.

Additionally, in the metal shell 5, there is a supporting member 51 having a cylindrical main body which supports the detecting element 2 from below, a filling member 52 that is filled into an upper portion of the supporting member 51 made of talc powder, and a sleeve 53 that presses the filling member 52 from above and the like.

A stepped portion 54 that protrudes inward is provided at an inner periphery on the side of a lower end of the metal shell 5. Also, the supporting member 51 is locked to the stepped portion 54 via packing 55, so that the detecting element 2 is supported from below. Additionally, the filling member 52 is arranged between the inner peripheral surface of the metal shell 5 and the outer peripheral surface of the detecting element 2 above the supporting member 51. Moreover, an upper end of the metal shell 5 is crimped inward (downward) in a state in which the cylindrical sleeve 53 and packing 56 are sequentially and coaxially inserted above the filling member 52. Consequently, the filling member 52 is filled under pressure so as to firmly fix the detecting element 2 to the metal shell 5. Additionally, metallic double protectors 57 and 58 covering the protruding portion of the detecting element 2 and having a plurality of openings are attached by welding to an outer periphery on the side of a lower end of the metal shell 5.

After a lower opening end of the outer tube 6 is fitted on the metal shell 5 so as to cover an upper opening of the metal shell 5, the lower opening end is welded from the outside to thereby mount the outer tube 6 on the metal shell 5.

Additionally, an insulating separator 7 formed of ceramic in a tubular shape is inserted into the vicinity of a rear end opening 61 in the outer tube 6. The separator 7 has an outwardly protruding flange portion 71 on an outer peripheral surface in the vicinity of the axial center thereof. Further, the separator 7 is held within the outer tube 6 in a state where a lower end surface of the flange portion 71 is locked to an upper portion of the outer tube 6 as the outer tube 6 is crimped from the outside.

Moreover, the rear end opening 61 of the outer tube 6 is provided with a seal unit 10 that prevents moisture or oil from entering inside the oxygen sensor 1. Further, outside lead wires 21 and 22 respectively connected to electrodes of the detecting element 2 and a pair of lead wires (not shown) connected to the ceramic heater 3 are pulled outside through the insertion holes 42 of the seal unit 10.

As shown in FIG. 2, the seal unit 10 includes a cylindrical grommet 11 that blocks the rear end opening 61 of the outer tube 6, a holding inner tube 12 that can be fitted into a through hole 41 passing through the center of the grommet 11 in an axial direction, a ventilation filter 13 that blocks a rear end opening 36 of the holding inner tube 12, a holding outer tube 14 that protects the ventilation filter 13, and a rubber packing 15 for preventing moisture from entering from the outside.

Among these, the grommet 11 is made of a fluororubber, and is formed with the above described through hole 41 and four insertion holes 42 (two are shown in FIGS. 1 and 2) for allowing the lead wires 21 and 22 and the lead wire for a heater to pass therethrough. In addition, the four insertion holes 42 are arranged so as to surround the through hole 41 which is arranged in the center thereof.

Additionally, the holding inner tube 12 includes a leading end portion 37 arranged within the through hole 41, and a rear end portion 38 protruding from a rear end surface 30 of the grommet 11. Moreover, the leading end of the holding inner tube 12 is provided with a locking portion 39 to prevent it from separating from the grommet 11.

Additionally, the ventilation filter 13 is configured, for example, as a ventilation filter that prevents the permeation of liquid composed mainly of water, such as droplets, and allows the permeation of gas (air, steam, etc.) by a porous fibrous structure (for example, trade name: Gore-Tex (Japan Gore-Tex, Inc.)) obtained by stretching a non-baked compact of polytetrafluoroethylene (PTFE) in a uniaxial direction at a heating temperature higher than the melting point of PTFE.

The ventilation filter 13 includes a filter blocking portion 23 that blocks the rear end opening 36 of the holding inner tube 12, and a filter tubular portion 24 that extends to the leading end side from a peripheral edge of the filter blocking portion 23 and surrounds the rear end portion 38 of the holding inner tube 12 in a peripheral direction.

Additionally, the holding outer tube 14 is formed in the shape of a close-end tube having an outer tube blocking portion 31 and an outer tube tubular portion 32. The outer tube blocking portion 31 in the holding outer tube 14 can be formed with a size sufficient to block the filter blocking portion 23 of the ventilation filter 13. Additionally, as shown in FIGS. 2 and 3, the outer tube blocking portion 31 is formed with a plurality of ventilation holes 33 having a sufficiently smaller opening area compared with the rear end opening 36 of the holding inner tube 12. Accordingly, the opening area of the rear end opening 36 of the holding inner tube 12 is larger than the total opening area of the plurality of ventilation holes 33.

The outer tube tubular portion 32 has a crimping portion 26 that is crimped toward the holding inner tube 12 via the filter tubular portion 24.

Additionally, the rubber packing 15 is formed in a cylindrical shape having a diameter allowing it to be brought into close contact with the outer peripheral surface of the holding inner tube 12. In this manner, the rubber packing 15 covers the holding inner tube 12 at a position corresponding to the crimping portion 26.

The seal unit 10 is formed by assembling the grommet 11, the holding inner tube 12, the ventilation filter 13, the holding outer tube 14 and the rubber packing 15, for example, as described below.

First, the cylindrical rubber packing 15 is placed on the holding inner tube 12 so as to cover the outer peripheral surface of the rear end portion 38 of the holding inner tube 12. Next, the ventilation filter 13 is placed on the holding inner tube 12 so that the ventilation filter 13 covers the outer peripheral surface of the rear end portion 38 and the rear end opening 36 in the holding inner tube 12. Additionally, the holding outer tube 14 is placed on the ventilation filter 13 so that the outer tube blocking portion 31 covers the holding inner tube 12, and the outer tube tubular portion 32 surrounds the outer peripheral surface of the rear end portion 38 of the holding inner tube 12.

This causes the rubber packing 15 and the ventilation filter 13 to be sandwiched between the rear end portion 38 of the holding inner tube 12 and the outer tube tubular portion 32 of the holding outer tube 14. In this state, the crimping portion 26 is formed by crimping in the radial direction via the outer tube tubular portion 32 of the holding outer tube 14. In this way, the outer tube tubular portion 32 and the ventilation filter 13 of the holding outer tube 14 are brought into close contact with each other, the ventilation filter 13 and the rubber packing 15 are brought into close contact with each other, and the ventilation filter 13 is fixed so as to block the rear end opening 36.

Thereafter, the holding inner tube 12 is inserted into the through hole 41 in the grommet 11 to form the seal unit 10.

Then, the seal unit 10 thus formed is arranged inside the rear end opening 61 of the outer tube 6, and the grommet 11 is crimped via the outer tube 6 in the radial direction. In this way, the outer tube 6 and the grommet 11 are brought into close contact with each other, to thereby ensure a more reliable seal. Then, air from the outside is introduced into the reference gas space via the ventilation path formed inside the holding inner tube 12 while maintaining the permeability and waterproofing property imparted by the ventilation filter 13.

In the oxygen sensor 1 configured in this way, the ventilation filter 13 having permeability and a waterproofing property is provided with the filter blocking portion 23 that blocks the rear end opening 36 of the holding inner tube 12. In this way, ambient air can be introduced into the inside of the sensor via the ventilation filter 13, without allowing moisture to pass to the inside of the sensor through the ventilation filter 13.

The ventilation filter 13 is also provided with a filter tubular portion 24 that surrounds the outer peripheral surface of the rear end portion 38 of the holding inner tube 12 that protrudes from the grommet 11 in the peripheral direction. That is, the end of the ventilation filter 13 is set outside the through hole 41 in the grommet 11. For this reason, moisture adhering to the surface (also referred to herein as the surface of the ventilation filter) of the ventilation filter 13 that faces the holding outer tube 14 does not enter the through hole 41 in the grommet 11 even if the moisture moves along the surface of the ventilation filter 13.

Additionally, the outer tube tubular portion 32 provided in the holding outer tube 14 surrounds the filter tubular portion 24 in the peripheral direction. That is, the outer tube tubular portion 32 is also arranged at the rear end portion 38 of the holding inner tube 12 that protrudes from the grommet 11, and there is no space formed that is blocked from the outside by the holding outer tube 14 and the grommet 11. Therefore, even if moisture adhering to the ventilation filter 13 runs along the surface of the ventilation filter 13, moisture is prevented from turning around at the end of the ventilation filter 13, reaching the rear end opening of the through hole 41, and entering the oxygen sensor 1.

The above configuration can prevent moisture adhering to the ventilation filter 13 from entering the oxygen sensor 1.

In addition, the outer tube blocking portion 31 of the holding outer tube 14 is formed with the ventilation hole 33. For this reason, even if the outer tube blocking portion 31 of the holding outer tube 14 covers the surface on the side of the rear end of the ventilation filter 13, introduction of ambient air into the oxygen sensor 1 via the ventilation filter 13 is secured.

Additionally, the outer tube tubular portion 32 is provided with the crimping portion 26 crimped in the peripheral direction toward the rear end portion 38 of the holding inner tube 12 via the filter tubular portion 24.

For this reason, there is no gap formed by the crimping portion 26 between the ventilation filter 13 and the holding outer tube 14. Therefore, since the crimping portion 26 is formed such that there is no path along which moisture moves even if moisture adhering to the surface of the ventilation filter 13 moves along the surface of the ventilation filter 13, the moisture is prevented from turning around at the end of the ventilation filter 13. Also, the moisture is prevented from reaching the rear end opening of the through hole 41 through a gap between the rear surface of the ventilation filter 13 and the holding inner tube 12.

Additionally, the rubber packing 15 is arranged between the ventilation filter 13 and the rear end portion 38 of the holding inner tube 12. For this reason, the outer tube tubular portion 32 is formed with the crimping portion 26, so that the rubber packing 15 arranged between the filter tubular portion 24 and the rear end portion 38 of the holding inner tube 12 can fill the gap between the filter tubular portion 24 and the rear end portion 38 of the holding inner tube 12. This can keep moisture, which covers the outer tube tubular portion 32 directly from the outside, from entering the oxygen sensor 1 through the gap between the rear surface of the ventilation filter 13 and the holding inner tube 12 from the end of the outer tube tubular portion 32.

In the embodiment described above, the oxygen sensor 1 corresponds to the sensor of the invention, the grommet 11 corresponds to the first elastic member of the invention, and the rubber packing 15 corresponds to the second elastic member of the invention.

Second Embodiment

Hereinafter, a second embodiment of the invention will be described with reference to the drawings. In addition, only portions that are different from those of the first embodiment will be described in the second embodiment.

Figure 4:
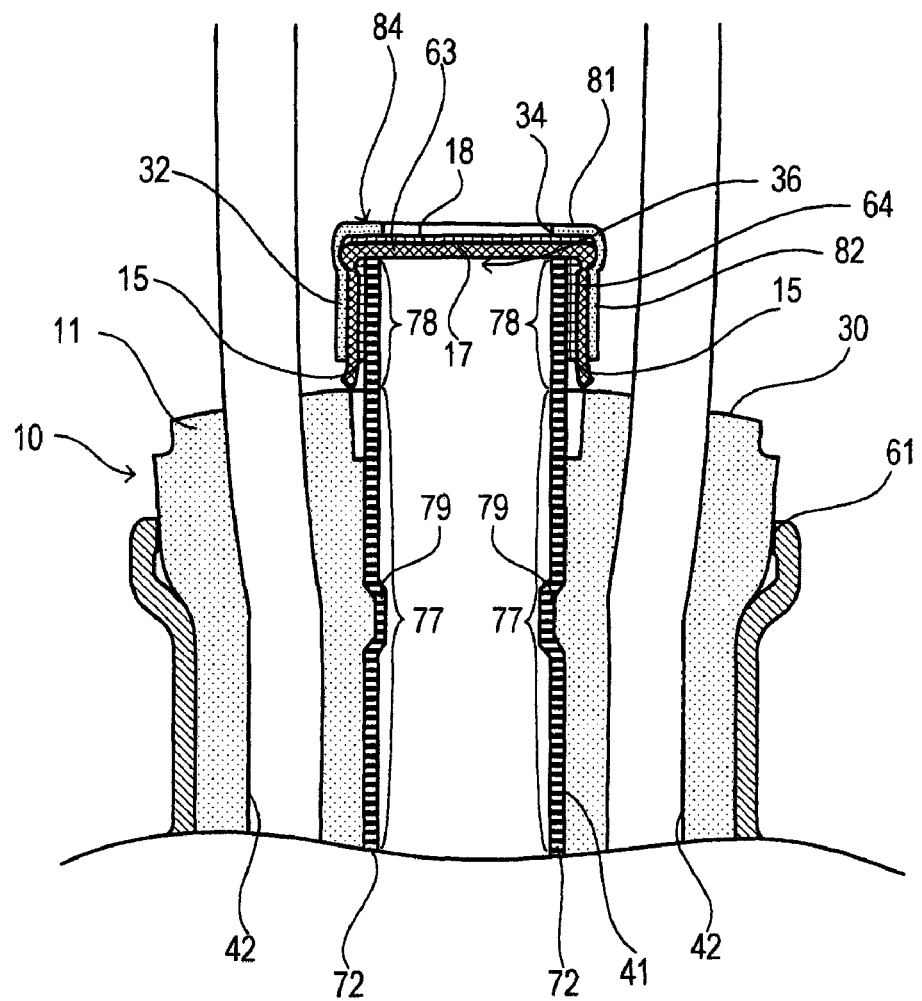
FIG. 4 is a sectional view showing the configuration of the seal unit 10 of a second embodiment.
Figure 5:
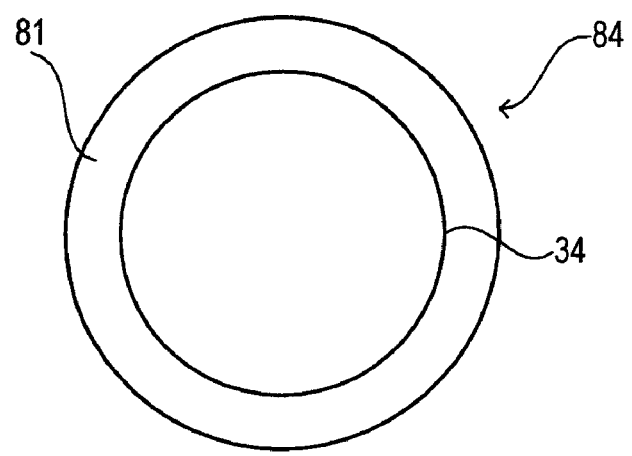
FIG. 5 is a plan view of a holding outer tube 84 of a second embodiment.

FIG. 4 is a sectional view showing the configuration of the seal unit 10 of the second embodiment, and FIG. 5 is a plan view of the holding outer tube 14 of the second embodiment. As shown in FIG. 4, the second embodiment differs from the first embodiment in that a holding inner tube 72, a ventilation filter 17, and a holding outer tube 84 are included instead of the holding inner tube 12, the ventilation filter 13, and the holding outer tube 14. Also, a mesh 18 is added.

First, instead of a locking portion 39 formed on the holding inner tube 12 as shown in FIG. 2, a diameter-reduced portion 79 is formed at a leading end portion 77 of the holding inner tube 72. A function of preventing the holding inner tube 12 from falling out or separating from the grommet 11 is achieved as the grommet 11 enters the diameter-reduced portion 79.

Additionally, the holding outer tube 84 of the second embodiment is the same as the holding outer tube 14 of the first embodiment, except that one ventilation hole 34 is formed instead of a plurality of ventilation holes 33. In addition, in this embodiment, an opening of the ventilation hole 34 is formed in a circular shape having a diameter approximately equal to that of the rear end opening 36 of the holding inner tube 72 (see FIG. 5).

Additionally, the ventilation filter 17 protrudes from an end edge of the outer tube tubular portion 32 of the holding outer tube 84, as shown in FIG. 4, in a state where the seal unit 10 is formed by assembling the grommet 11, the holding inner tube 72, the ventilation filter 17, the holding outer tube 84 and the rubber packing 15.

Additionally, the mesh 18 is a sheet member that is formed in a mesh shape, and is formed, for example, from a SUS mesh in this embodiment. The mesh 18 is arranged between an outer tube blocking portion 81 of the holding outer tube 84 and the ventilation filter 17 so as to cover the filter blocking portion 63.

In the oxygen sensor 1 configured in this way, the ventilation filter 17 can be spared from damage by an external force because the surface of the ventilation filter 17 is covered with the mesh 18. In addition, the openings in mesh 18 secure introduction of ambient air into the oxygen sensor 1 via the ventilation filter 17.

Additionally, a filter tubular portion 64 of the ventilation filter 17 is exposed closer to the leading end side than the leading end of the outer tube tubular portion 82. For this reason, once crimped as shown in FIG. 2, the crimping condition of the outer tubular portion 82 by action of the crimping portion 26 with the filter tubular portion 64 therebetween is readily determined.

Although two embodiments of the invention have been described above, the invention is not limited thereto, and various forms and modifications can be adopted within the spirit and scope of the invention. For example, although a seal unit 10 for use in an oxygen sensor is shown in the above embodiments, the invention is not limited to an oxygen sensor. For example, a sensor may be adopted which is of a type in which ambient air is introduced inside the sensor via a ventilation filter.

Additionally, although the tubular detecting element 2 has been adopted in the above embodiments, the invention is not limited thereto, and a plate-like detecting element may be employed.

Additionally, the holding outer tube 14 may be fixed to the holding inner tube 12 by welding together the outer tube tubular portion 32 of the holding outer tube 14 and the rear end 38 of the holding inner tube 12.

According to an illustrative aspect, the present invention provides a sensor comprising: a tubular casing that holds a detecting element extending in an axial direction so as to expose a leading end of the detecting element to a gas to be measured, the tubular casing extending in the axial direction and having an open rear end; and a first elastic member that having a through hole that is provided along the axial direction so as to introduce ambient air into the casing and disposed so as to block a rear end opening of the casing, wherein the sensor includes: a holding inner tube that closely contacts an inner peripheral surface of the through hole of the first elastic member, the holding inner tube having a rear end portion that protrudes from a rear end of the first elastic member; a ventilation filter having permeability and a waterproofing property, the ventilation filter including a filter blocking portion that blocks a rear end opening of the holding inner tube, and a filter tubular portion connected to the filter blocking portion and surrounding at least a portion of an outer peripheral surface of the rear end portion of the holding inner tube in the peripheral direction; and a holding outer tube that includes a ventilation hole that is provided along the axial direction, an outer tube blocking portion covering the filter blocking portion, and an outer tube tubular portion connected to the outer tube blocking portion and surrounding at least a portion of the filter tubular portion in the peripheral direction.

In a sensor thus configured, the ventilation filter that has permeability and a waterproofing property is provided with the filter blocking portion that blocks the rear end opening of the holding inner tube. In this way, ambient air can be introduced inside the sensor via the ventilation filter, without allowing moisture to pass to the inside of the sensor through the ventilation filter.

The ventilation filter is also provided with the filter tubular portion that surrounds the outer peripheral surface of the rear end portion of the holding inner tube that protrudes from the first elastic member in the peripheral direction. That is, the end of the ventilation filter is set outside the through hole in the first elastic member. For this reason, moisture adhering to the surface (also referred to as the surface of the ventilation filter) of the ventilation filter that faces the holding outer tube does not enter the through hole of the first elastic member even if the moisture moves along the surface of the ventilation filter.

Additionally, the outer tube tubular portion provided in the holding outer tube surrounds the filter tubular portion in the peripheral direction. That is, the outer tube tubular portion is also arranged at the rear end of the holding inner tube that protrudes from the first elastic member, and there is no space formed that is blocked from the outside by the holding outer tube (the outer tube tubular portion) and the first elastic member. Therefore, even if moisture adhering to the ventilation filter runs along the surface of the ventilation filter, this configuration prevents the moisture from turning around at the end of the ventilation filter, reaching the rear end opening of the through hole, and entering the sensor.

The above configuration can prevent moisture adhering to the ventilation filter from entering the sensor. In addition, the holding inner tube only has to be brought into close contact with the inner peripheral surface of the through hole in the first elastic member. The outer shape of the holding inner tube may be made slightly larger than the through hole and the holding inner tube may be pressed-fitted into the through hole. Alternatively, the outer shape of the holding inner tube may be made equal to or slightly smaller than the through hole, and both the holding inner tube and the through hole may be brought into close contact with each other by the elasticity of the first elastic member.

Additionally, the filter tubular portion may surround the entire outer peripheral surface of the rear end portion of the holding inner tube in the peripheral direction, or may surround a portion (specifically, the rear end side of the rear end portion of the holding inner tube) in the peripheral direction. Moreover, although the outer tube tubular portion may surround the entire rear end portion of the holding inner tube in the peripheral direction, surrounding a portion (specifically, the rear end side of the rear end portion of the holding inner tube) in the peripheral direction means that the outer tube tubular portion does not come into contact with the rear end surface of the first elastic member. As a result, durability can be maintained without damaging the first elastic member.

Further, according to a preferred embodiment of the invention, the outer tube tubular portion has a crimping portion that is crimped in a peripheral direction toward the rear end portion of the holding inner tube via the filter tubular portion.

There is no gap formed between the ventilation filter and the holding outer tube due to the crimping portion being provided in the outer tube tubular portion. Accordingly, even if moisture adhering to the surface of the ventilation filter moves along the surface of the ventilation filter, the crimping portion is formed such that there is no path along which the moisture can move. Consequently, the moisture is prevented from turning around at the end of the ventilation filter, and is also prevented from reaching the rear end opening of the through hole through a gap between the rear surface of the ventilation filter and the holding inner tube.

In addition, although the crimping portion may be formed by crimping one spot on the outer tube tubular portion in the peripheral direction, it is possible to further kept moisture from entering the sensor if a plurality of spots is crimped in the peripheral direction.

Further, according to another preferred embodiment of the invention, a second elastic member that has a waterproofing property is disposed between the filter tubular portion corresponding to at least the crimping portion, and the rear end portion of the holding inner tube.

In a sensor configured in this way, the outer tube tubular portion is formed with the crimping portion, so that the second elastic member arranged between the filter tubular portion and the rear end portion of the holding inner tube can fill the gap between the filter tubular portion and the rear end portion of the holding inner tube. This configuration can prevent moisture, which covers the outer tube tubular portion directly from the outside, from entering the sensor through the gap between the rear surface of the ventilation filter and the holding inner tube from the end of the outer tube tubular portion.

In addition, the second elastic member only has to be at a position corresponding to the crimping portion, or may cover the entire outer periphery of the rear end portion of the holding inner tube.

Further, according to yet another preferred embodiment of the invention, the minimum area of the through hole is greater than the minimum area of the ventilation hole.

When ambient air is introduced into the inside of the sensor via the ventilation filter, the amount of the ambient air that reaches the ventilation filter depends on the minimum area of the ventilation hole formed in the outer tube blocking portion. On the other hand, the amount of ambient air that passes the ventilation filter and flows to the inside (interior) of the sensor depends on the minimum area of the through hole formed in the holding inner tube.

Thus, the gas that has passed through the ventilation filter via the ventilation hole smoothly flows into the inside of the sensor by making the minimum area of the through hole greater than the minimum area of the ventilation hole.

In addition, the minimum area of the ventilation hole or the minimum area of the through hole means the area of a hole that becomes the smallest when the ventilation hole or the through hole is viewed in the axial direction. For example, the minimum area refers to the area of a hole at a leading end where the ventilation hole or the through hole is the smallest in the case where the ventilation hole or the through hole is formed in a cone shape that becomes narrower toward the leading end side.

Additionally, a plurality of the ventilation holes or through holes may be provided. If plural ventilation holes or through holes are provided, the minimum area of the ventilation hole or the minimum area of the through hole corresponds to the total of the minimum areas of the respective ventilation holes or through holes.

Further, according to yet another preferred embodiment of the invention, the sensor further comprises, a net-like sheet member that is provided between the filter blocking portion and the outer tube blocking portion, the net-like sheet member having a higher Vickers hardness than the ventilation filter.

In a sensor thus configured, the ventilation filter can be spared from damage by an external force. This is because the surface of the ventilation filter is covered with the sheet member (also referred to as a net-like sheet member) that is formed in a mesh shape. Since the net-like sheet member is formed with openings created in the mesh, introduction of ambient air into the sensor via the ventilation filter is secured.

Further, according to yet another preferred embodiment of the invention, the filter tubular portion is exposed closer to a leading end side than the leading end of the outer tube tubular portion.

In a sensor thus configured, the crimping condition of the outer tube tubular portion by action of the crimping portion with the filter tubular portion therebetween is readily determined.

The present application claims priority from Japanese Patent Application No. 2008-186025 filed on Jul. 17, 2008, and from Japanese Patent Application No. 2009-133243 filed on Jun. 2, 2009, the disclosures of which are incorporated herein by reference in their entirety.

What is claimed is:

1. A sensor comprising:
a tubular casing that holds a detecting element extending in an axial direction so as to expose a leading end of the detecting element to a gas to be measured, the tubular casing extending in the axial direction and having an open rear end; and
a first elastic member having a through hole that is provided along the axial direction so as to introduce ambient air into the casing and disposed so as to block the rear end opening of the casing,
wherein the sensor further includes:
a holding inner tube in close contact with an inner peripheral surface of the through hole of the first elastic member, the holding inner tube having a rear end portion that protrudes from a rear end of the first elastic member;
a ventilation filter having permeability and a waterproofing property, the ventilation filter including:
a filter blocking portion that blocks a rear end opening of the holding inner tube; and
a filter tubular portion connected to the filter blocking portion and surrounding at least a portion of an outer peripheral surface of the rear end portion of the holding inner tube in the peripheral direction, the filter tubular portion being entirely disposed away from and to the rear end of the first elastic member; and
a holding outer tube that includes:
a ventilation hole that is provided along the axial direction;
an outer tube blocking portion covering the filter blocking portion; and
an outer tube tubular portion connected to the outer tube blocking portion and surrounding at least a portion of the filter tubular portion in the peripheral direction, the outer tube tubular portion being entirely disposed away from and to the rear end of the first elastic member.

2. The sensor according to claim 1,
wherein the outer tube tubular portion has a crimping portion that is crimped in a peripheral direction toward the rear end portion of the holding inner tube via the filter tubular portion.

3. The sensor according to claim 1,
wherein the minimum area of the through hole is greater than the minimum area of the ventilation hole.

4. The sensor according to claim 1, further comprising,
a net-like sheet member is provided between the filter blocking portion and the outer tube blocking portion, the net-like sheet member having a higher Vickers hardness than the ventilation filter.

5. The sensor according to claim 1,
wherein the filter tubular portion is exposed closer to a leading end side than the leading end of the outer tube tubular portion.

6. A sensor comprising:
a tubular casing that holds a detecting element extending in an axial direction so as to expose a leading end of the detecting element to a gas to be measured, the tubular casing extending in the axial direction and having an open rear end; and
a first elastic member having a through hole that is provided along the axial direction so as to introduce ambient air into the casing and disposed so as to block the rear end opening of the casing,
wherein the sensor further includes:
a holding inner tube in close contact with an inner peripheral surface of the through hole of the first elastic member, the holding inner tube having a rear end portion that protrudes from a rear end of the first elastic member;
a ventilation filter having permeability and a waterproofing property, the ventilation filter including:
a filter blocking portion that blocks a rear end opening of the holding inner tube; and a filter tubular portion connected to the filter blocking portion and surrounding at least a portion of an outer peripheral surface of the rear end portion of the holding inner tube in the peripheral direction; and a holding outer tube that includes:

a ventilation hole that is provided along the axial direction;

an outer tube blocking portion covering the filter blocking portion; and an outer tube tubular portion connected to the outer tube blocking portion and surrounding at least a portion of the filter tubular portion in the peripheral direction, wherein the outer tube tubular portion has a crimping portion that is crimped in a peripheral direction toward the rear end portion of the holding inner tube via the filter tubular portion.

7. The sensor according to claim 6, wherein a second elastic member that has a waterproofing property is disposed between the filter tubular portion corresponding to at least the crimping portion and the rear end portion of the holding inner tube.

* * * * *